(12) United States Patent
Kahn

(10) Patent No.: US 8,365,604 B2
(45) Date of Patent: Feb. 5, 2013

(54) APPARATUS FOR AND METHOD OF DETECTING DEFECTS IN A RAIL JOINT BAR

(75) Inventor: Jason M. Kahn, Savannah, MO (US)

(73) Assignee: Herzog Services, Inc., St. Joseph, MO (US)

( * ) Notice: Subject to any disclaimer, the term of this patent is extended or adjusted under 35 U.S.C. 154(b) by 352 days.

(21) Appl. No.: 12/872,460

(22) Filed: Aug. 31, 2010

(65) Prior Publication Data

US 2011/0209549 A1   Sep. 1, 2011

Related U.S. Application Data

(60) Provisional application No. 61/238,484, filed on Aug. 31, 2009.

(51) Int. Cl.
*G01N 29/04* (2006.01)
*G01N 33/00* (2006.01)

(52) U.S. Cl. .......................... 73/636; 73/865.8

(58) Field of Classification Search ............. 73/636, 73/602, 624, 633, 634, 643, 865.8
See application file for complete search history.

(56) References Cited

U.S. PATENT DOCUMENTS

| | | | |
|---|---|---|---|
| 2,546,256 A * | 3/1951 | Drake | 324/218 |
| 2,645,938 A | 7/1953 | Billstein | |
| 2,736,193 A | 2/1956 | Van Valkenburg et al. | |
| 3,028,751 A | 4/1962 | Joy | |
| 3,593,841 A * | 7/1971 | Leow | 198/806 |
| 4,143,553 A | 3/1979 | Martens et al. | |
| 4,165,648 A * | 8/1979 | Pagano | 73/625 |
| 4,454,624 A * | 6/1984 | Vandermer | 15/229.13 |
| 4,487,071 A | 12/1984 | Pagano et al. | |
| 4,593,569 A | 6/1986 | Joy | |
| 4,662,224 A | 5/1987 | Turbe | |
| 5,031,458 A | 7/1991 | Young et al. | |
| 6,055,862 A | 5/2000 | Martens | |
| 6,476,603 B2 | 11/2002 | Clark et al. | |
| 6,571,636 B1 | 6/2003 | McWhorter | |
| 6,581,466 B1 | 6/2003 | Costley et al. | |
| 6,594,591 B2 | 7/2003 | Clark et al. | |
| 6,600,999 B2 | 7/2003 | Clark et al. | |
| 6,658,939 B2 | 12/2003 | Georgeson et al. | |
| 6,742,392 B2 | 6/2004 | Gilmore et al. | |
| 6,862,936 B2 | 3/2005 | Kenderian et al. | |
| 6,945,114 B2 | 9/2005 | Kenderian et al. | |
| 7,197,932 B2 | 4/2007 | Sakai et al. | |
| 7,213,459 B2 | 5/2007 | Sengupta | |
| 7,484,413 B2 | 2/2009 | Georgeson et al. | |
| 7,755,660 B2 | 7/2010 | Nejikovsky et al. | |
| 2009/0266166 A1 * | 10/2009 | Pagano | 73/636 |

(Continued)

OTHER PUBLICATIONS

Ensco, Inc., "Automated Joint Bar Inspection System," Federal Research Federal Railroad Administration.

(Continued)

*Primary Examiner* — J M Saint Surin
(74) *Attorney, Agent, or Firm* — Erickson, Kernell, Derusseau & Kleypas, LLC

(57) ABSTRACT

An apparatus and method for inspecting a rail joint bar transported along a railway rail by an inspection vehicle is provided. The apparatus and method includes a pair of ultrasonic transducers housed in liquid-filled wheels. The wheels are positionable for a stored position to a measurement position in rolling contact with the vehicle surfaces of the rail joint bars on each side of the rail. The ultrasonic transducer transmits a signal into the rail joint bar and the reflected signal is detected by the transducer and analyzed to identify flaws in the rail joint bar.

18 Claims, 3 Drawing Sheets

U.S. PATENT DOCUMENTS

2012/0218868 A1* 8/2012 Kahn et al. .................. 367/99

OTHER PUBLICATIONS

U. S. Department of Transportation, Federal Railroad Administration, "Research Results: Video System for Joint Bar Inspection," Mar. 2006, RR06-03.

F. Lanza Di Scalea, P, Rizzo, S. Cocia, I. Bartoili, M. Fateh, E. Viola and G. Pascale, "Non-Contact Ultrasonic Inspection of Rails and Signal Processing for Automatic Defect Detection and Classification," Insight vol. 47, No. 6, Jun. 2005, pp. 1-8.

Boris Nejikovsky, Gary Carr, Christian Diaz, William Jordan, Xavier Gibert-Serra, Ali Tajaddini, "Automated Joint Bar Inspection Using High Speed Cameras," presentation to American Railway Engineering and Maintenance-of-Way Association, Sep. 29, 2005.

Xavier Gibert-Serra, Andrea Berry, Christian Diaz, William Jordan, Boris Nejikovsky, Ali Tajaddini, "A Machine Vision System for Automated Joint Bar Inspection from a Moving Rail Vehicle," 2007 ASME/ IEEE Joint Rail Conference & Internal Combustion Engine Spring Technical Conference, Mar. 13-16, 2007, JRCICE2007-40039.

Arema, "Basic Track," Chapter 3, pp. 69, 74-75, 78-80, 2003.

* cited by examiner

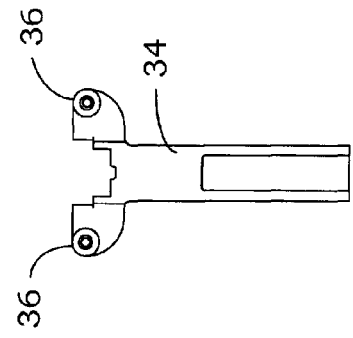
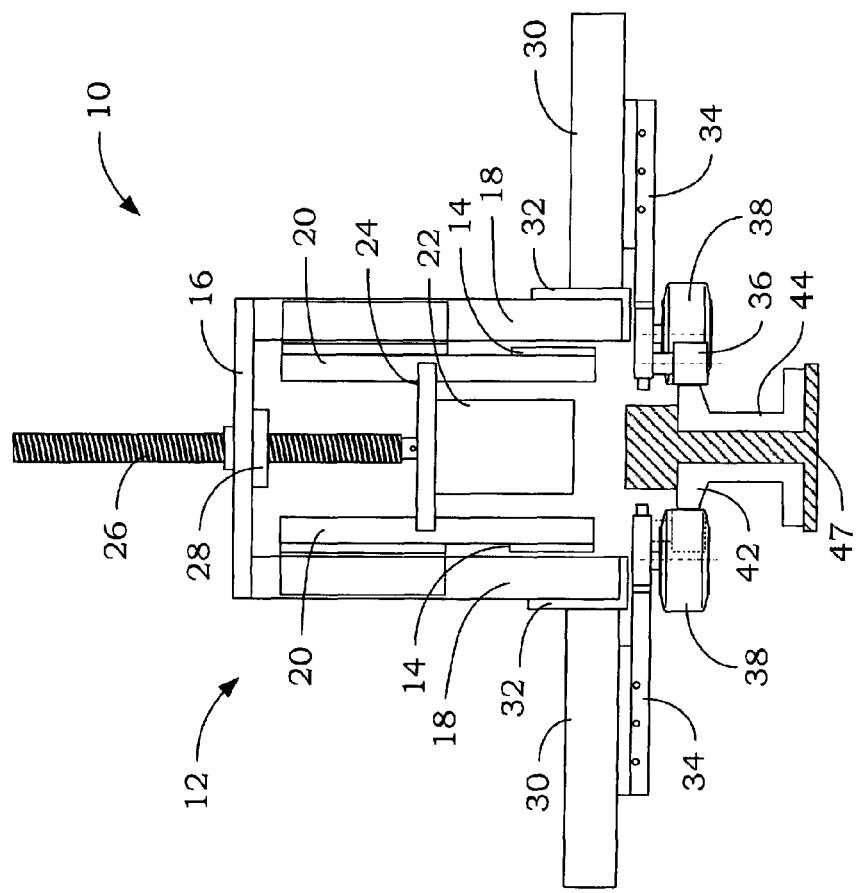

APPARATUS FOR AND METHOD OF DETECTING DEFECTS IN A RAIL JOINT BAR

CROSS-REFERENCE TO RELATED APPLICATIONS

This application claims the benefit of co-pending application Ser. No. 61/238,484, filed on Aug. 31, 2009, entitled APPARATUS FOR METHOD OF DETECTING DEFECTS IN A RAIL JOINT BAR.

FIELD

The present invention relates generally to an apparatus for and method of detecting defects in a rail joint bar and, more particularly, to a mobile apparatus for and method of performing nondestructive-type testing using ultrasonic transducers to detect flaws and defects in a rail joint bar.

BACKGROUND

The United States Federal Railroad Administration has published statistics which indicate that train accidents caused by track failures including rail, joint bars and anchoring resulted in approximately 2700 derailments from 1992 to 2002. The primary cause of these track failures is a transverse defect and fissure running perpendicular to the rail running direction in the rail and rail bar joint.

A pair of rail joint bars holds the two ends of a rail in place and act as a bridge between the rail ends. The rail joint bars prevent lateral and vertical movement of the rail ends and permit longitudinal movement of the rails to accommodate expanding and contracting. Bolts extending through holes in the joint bars and the rail ends secure the rail ends together. Rail joint bars are typically 24 or 36 inches long with four or six bolt holes, respectively.

Various methods of rail inspection include magnetic, contact, ultrasonic and video. One such video system is the Automated Optical Joint Bar Inspection System developed by ENSCO, Inc. in cooperation with the Federal Railroad Administration. One such ultrasonic system is disclosed in U.S. Pat. No. 6,055,862 entitled "Method of and Apparatus for Detecting, Identifying and Recording the Location of Defects in a Railway Rail," which is incorporated herein by reference.

One problem with video inspection systems is the inability to see into the rail joint bar and the area of the rail joint bar hidden under the head of the rail. Further, the most common failure of rail joint bars begins in an area centrally located within the bar. Video systems are also susceptible to false readings because of debris, rust and discoloration or streaks on the joint bar.

Ultrasonic testing of rails is performed with ultrasonic transducers housed in a liquid-filled wheel. The wheel rides along the top of the rail head while the transducers transmit ultrasonic waves into the rail head and receive reflected waves from the rail head. The orientation of the transducers and the wave path are used to identify defects in the rail head and web. However, the wave cannot pass from the rail head into the rail joint bar.

SUMMARY

The present invention provides an apparatus for and method of detecting defects in a rail joint bar. The apparatus includes a pair of opposed liquid-filled transducer wheels which are repositionable laterally and vertically. Each wheel is protected by a pair of idler rollers one on opposite sides of the wheel to ensure that the wheel is in contact with the head of the rail joint bar for measurement.

Pneumatic or hydraulic cylinders or electromechanical devices may be used to reposition the wheels laterally and vertically to align the wheels with the joint bar head and to move the wheel assembly away from rail obstructions. The apparatus is mounted to a carriage assembly which is secured to a rail inspection vehicle.

BRIEF DESCRIPTION OF THE DRAWINGS

FIG. 2 is a front view of the cradle assembly of the rail joint bar inspection device.

FIG. 4 is a bottom plan view of the idler arm of the rail joint bar inspection device.

DETAILED DESCRIPTION

Figure 1:
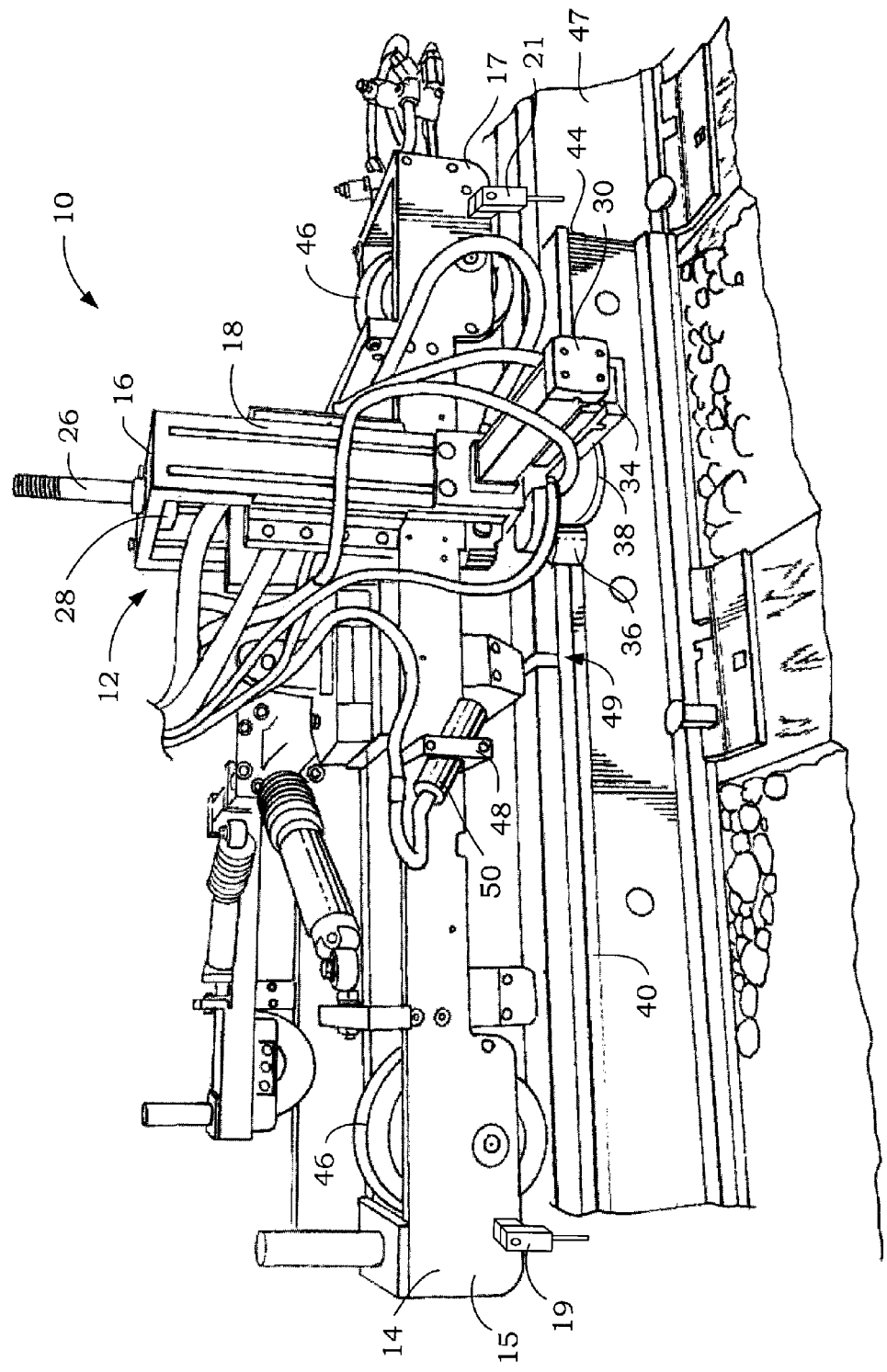
FIG. 1 is a perspective side view of the rail joint bar inspection device of the present invention.
Figure 3:
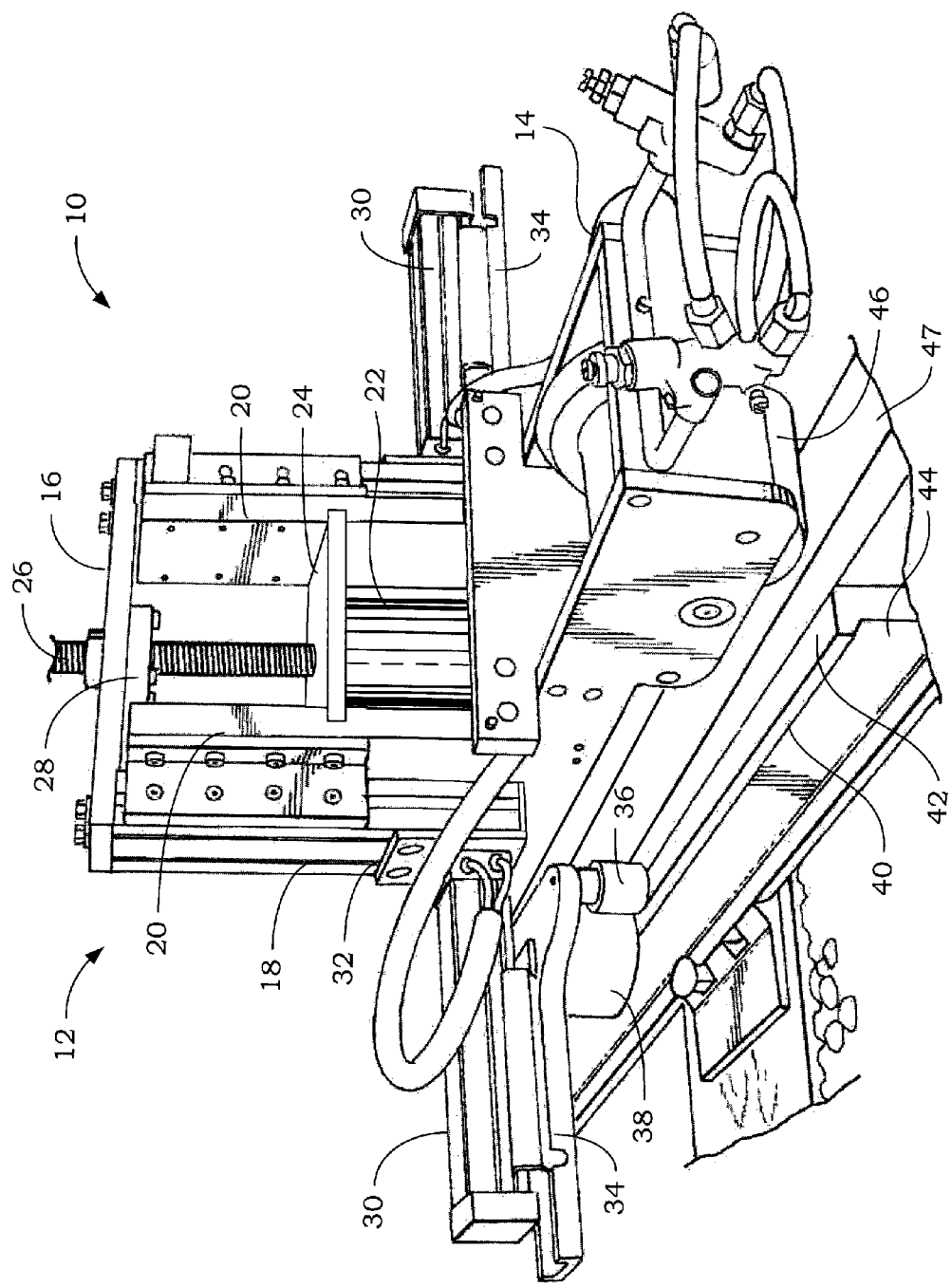
FIG. 3 is a perspective front view of the rail joint bar inspection device.

As required, detailed embodiments of the present invention are disclosed herein. However, it is to be understood that the disclosed embodiments are merely exemplary of the invention that may be embodied in various and alternative forms. The drawings are not necessarily to scale, some features may be exaggerated or minimized to show details of particular components. Therefore, specific structural and functional details disclosed herein are not to be interpreted as limiting, but merely as a representative basis for the claims and/or as a representative basis for teaching one skilled in the art to variously employ the present invention.

Moreover, except where otherwise expressly indicated, all numerical quantities in this description and in the claims are to be understood as modified by the word "about" in describing the broader scope of this invention. Practice within the numerical limits stated is generally preferred. Also, unless expressly stated to the contrary, the description of a group or class of materials as suitable or preferred for a given purpose in connection with the invention implies that mixtures or combinations of any two or more members of the group or class may be equally suitable or preferred.

Referring to the drawings, a rail joint bar inspection device is generally indicated by reference numeral 10. Rail joint bar inspection device 10 includes a cradle 12 secured to a carriage 14. The cradle 12 is movable vertically in relationship to the carriage 14. The carriage 14 provides a platform for mounting the cradle 12 and related equipment.

The cradle 12 is generally an inverted U-shaped structure with a top plate 16 and a pair of legs 18 extending downwardly from the top plate 16. A pair of cradle to carriage interface plates 20 slidably secure the cradle 12 to the carriage 14. The cradle to interface plates 20 are secured to the carriage 14 and thus fixed to allow the cradle 12 to move in a vertical plane relative to the carriage 14. A motor 22 is mounted to a motor support 24, which is secured to the interface plates 20. The motor 22 drives a screw or threaded rod 26 which passes through a nut 28 which is welded to the top plate 16. As the motor 22 turns the screw 26, the cradle 12 moves up or down. It should be understood that other mechanisms for moving the cradle 12 may be used such as a pneumatic cylinder, solenoid or hydraulic cylinder, for example.

Extending outwardly from each cradle leg 18 is an actuator 30, which is mounted to the lower end of the respective cradle leg 18 with a bracket 32. In the preferred embodiment the actuator 30 may be a rod-less pneumatic cylinder with a one-inch bore and a two-inch stroke, however, other actuators such as motors, solenoids and hydraulic cylinders, for example, may be used. Slidably attached to each actuator 30 is an idler arm 34 which supports a pair of idler rollers 36 and a sensor assembly 38. The sensor assembly 38 is a liquid-filled wheel known in the art, which houses an ultrasonic transducer mounted at an angle between approximately 35 degrees to 55 degrees, and more particularly 37.5 degrees to 52.5 degrees to the outside vertical surface 40 of the head 42 of the rail joint bar 44. The ultrasonic transducer produces an ultrasonic beam that is transmitted in a horizontal plane. The width of the sensor assembly 38 may be minimized to avoid contact with bolt heads and nuts holding the rail joint bars 44 to the rails 47. In FIG. 2, the idler roller 36 on the left idler arm 34 is shown in broken lines to more clearly show the orientation of the sensor assembly 38 relative to the rail joint bar head 42 and vertical surface 40.

The idler rollers 36 limit the inward movement of the idler arm 30. When the idler rollers 36 are in contact with the vertical surface 40 of the rail joint bar head 42, the spacing between the ultrasonic transducer mounted within the sensor assembly 38 is maintained at an optimal and constant distance from the vertical surface 40.

The pair of carriages 14 is coupled to a rail inspection vehicle (not shown) which pushes or pulls the carriages 14 along a railway. Each carriage 14 includes a pair of rail wheels 46, which ride on the rails 47 and provide a stable reference plane for the cradle 12 and sensor assembly 38. At least one of the carriages 14 may also include a camera mount 48 to support a camera 50. The camera 50 may be used to help an operator identify a rail joint bar 44 and to position the cradle 12 and idler arms 34 relative to the rail joint bar head 42.

In a manual operation, the carriage 14 is pulled along a railway by an inspection vehicle. An operator riding in the inspection vehicle monitors a display (not shown) coupled to the camera 50. As the inspection vehicle approaches a rail joint bar 44, the operator energizes the motor 22 to turn the screw 26 in a direction to lower the cradle 12 to a height where the surface of the sensor assembly 38 is aligned in a horizontal plane perpendicular to the vertical surface 40 of the rail joint bar head 42. The operator also activates the actuators 30 to slide the idler arms 34 inwardly until the idler rollers 36 and sensor assemblies 38 are in contact with the rail joint bar head 42. As the sensor assemblies 38 roll along the vertical surface 40 the rail joint bar head 42, the ultrasonic transducers mounted within the sensor assembly 38 transmits an ultrasonic wave into the rail joint bar head 42. The return signal is received and analyzed to identify defects in the rail joint bar head 42 at an angle of approximately 35 degrees to 55 degrees, and preferably 37.5 degrees to 52.5 degrees relative to the vertical surfaces 40 of the rail joint bar head 42. When the sensor assembly 38 passes the end of the joint bar 44, the pressure may be released from the actuators 30 allowing the idler arms 34 to return to their initial or stored position translating the idler rollers 36 and sensor assemblies 38 away from the vertical surface 40 of the rail joint bar head 42. The motor 22 may also be reversed to turn the screw 26 to raise the cradle 12. This procedure may be repeated for each joint bar 44 encountered along the rails.

It should be understood that the cradle 12 need not be raised after reaching the end of a rail joint bar 44. It may be advantageous to leave the cradle 12 in the lowered position to minimize the time necessary for the sensor assembly 38 to initially contact a rail joint bar head 42 vertical surface 40. However, because the idler arms 30, idler rollers 36 and sensor assemblies 38 extend below the horizontal plane of the top surface of the rail head 47, it may be desirable to raise the cradle 12 to avoid damage to the inspection device 10 when approaching a crossing or switch, for example.

In an automatic operation, the leading end 15 and/or trailing end 17 of the carriage 14 may be equipped with limit, whisker, or optical switches/sensors 19 and 21, respectively, to detect the leading and/or trailing edges and thereby the presence of the rail joint bars 44. When the leading limit switch 19 encounters the leading edge of the rail joint bar head 42, the cradle 12 may be automatically lowered to a height where the surface of the sensor assembly 38 is aligned in a horizontal plane perpendicular to the vertical surface 40 of the rail joint bar head 42. The actuators may then be 30 actuated to slide the idler arms 30 inwardly until the idler rollers 36 and the sensor assemblies 38 engage the vertical surface 40 of the joint bar head 42. As the sensor assemblies 38 roll along the vertical surface 40 the rail joint bar head 42, the ultrasonic transducers mounted within the sensor assembly 38 transmits an ultrasonic wave into the rail joint bar head 42 at an angle of approximately 37.5° to 52.5° relative to the vertical surface 40 of the rail joint bar head 42. The return signal is received and analyzed to identify defects in the rail joint bar head 42. When the trailing limit switch 21 is disengaged from the rail joint bar head 42, the sensor assembly is automatically disengaged from the rail joint bar head 42 and the cradle 12 may be raised. Various combinations of video and electromechanical activation of the rail joint bar inspection device 10 may be used to control the movement of the sensor assembly 38 to inspect the rail joint bar head 42.

Because the majority of hairline fractures and other defects are found at the rail joint 49 between two rails 47, and the standard length of a rail joint bar 44 is 24 or 36 inches, the maximum time from the engagement of the leading limit switch 19 and contact of the sensor assembly 38 with the vertical surface 40 of the rail joint bar head 42 may be approximately X/2 divided by Y, where X is the length of the rail joint bar 44 and Y is the speed of the rail inspection vehicle. Preferably, the maximum time is X/4 divided by Y to ensure that the sensor assembly 38 is in contact well before passing the rail joint 49.

By way of example, suppose a rail inspection vehicle is traveling along a railway at ten miles per hour, or 177 inches per second. For the sensor assembly 38 to make contact within six inches of the front edge of the rail joint bar 44 it needs to move from a disengaged position to an engaged position within 0.034 seconds. Solenoids, air cylinders or hydraulic cylinders, for example, may be used to rapidly move the idler arm 30 and attached idler rollers 36 and sensor assembly 38 from a disengaged position to an engaged position.

It is to be understood that while certain forms of this invention have been illustrated and described, it is not limited thereto, except in so far as such limitations are included in the following claims and allowable equivalents thereof.

Having thus described the invention, what is claimed as new and desired to be secured by Letters Patent is:

1. An apparatus for inspecting joint bars having a head with an outside vertical surface and mounted on opposite sides of a rail, said apparatus comprising:

a carriage having at least one wheel for engaging the rail, a frame slidably mounted to said carriage, said frame having legs spaced apart to straddle the rail and joint bars mounted on opposite sides of the rail, a first actuator secured to said carriage and coupled to said frame for adjusting the frame vertically between a first position and a second position, second and third actuators one of each secured to opposite lower ends of said frame legs and each extending outwardly from said frame legs, a pair of idler arms one of each slidably mounted to said second and third actuators, said idler arms positionable horizontally between a first position and a second position, and each having a lower horizontal surface, a pair of sensor assemblies one of each rotatably secured to said lower horizontal surface of said idler arms, whereby when said frame is in said first position and said idler arms are in said first position, said sensor assemblies are in a stored position away from said rail and pair of joint bars, whereby when said frame is in said second position and said idler arms are in said second position, said sensor assemblies are engaged with the joint bars mounted on opposite sides of the rail.

2. The apparatus of claim 1 wherein said actuators are selected from the group consisting of a motor, a solenoid, a pneumatic cylinder and a hydraulic cylinder.

3. The apparatus of claim 1 wherein each of said sensor assemblies engage the vertical surface of the head of each joint bar.

4. The apparatus of claim 1 wherein said sensor assemblies include an ultrasonic transducer mounted in a liquid-filled wheel.

5. The apparatus of claim 4 wherein said ultrasonic transducer is mounted in said liquid-filled wheel in a horizontal plane generally perpendicular to the vertical surface of the head of the joint bar and at an angle between approximately 35 degrees and 55 degrees relative to the vertical surface of the head of the joint bar.

6. The apparatus of claim 4 wherein said ultrasonic transducer is mounted in said liquid-filled wheel in a horizontal plane generally perpendicular to the vertical surface of the head of the joint bar and at an angle between approximately 37.5 degrees and 52.5 degrees relative to the vertical surface of the head of the joint bar.

7. The apparatus of claim 4 further comprising two pairs of idler rollers one of each mounted to said lower horizontal surface of each of said idler arms on opposite sides of said liquid-filled wheel, each of said pair of idler rollers positioned to limit movement of said idler arms from said first position to said second position.

8. The apparatus of claim 1 further comprising a camera mounted to said carriage and directed toward the rail to identify the beginning and end of the joint bar.

9. The apparatus of claim 1 further comprising an edge detector mounted to said carriage to identify an end of a joint bar.

10. The apparatus of claim 9 wherein said edge detector is selected from a group consisting of a limit switch, a whisker switch, an optical switch and an infrared switch.

11. A method for inspecting a rail joint bar transported along a railway rail by an inspection vehicle comprising:
    detecting the presence of a rail joint bar,
    positioning a sensor assembly in rolling contact with said rail joint bar,
    emitting an ultrasonic beam from said sensor assembly into said rail joint bar at an angle relative to the contact surface of said rail joint bar,
    receiving a reflected ultrasonic signal by said sensor assembly and outputting a corresponding electrical signal,
    processing said electrical signal to detect signals indicative of a flaw in said rail joint bar, and
    repositioning said sensor assembly away from said rail joint bar.

12. The method of claim 11 wherein said detecting step includes detecting the leading edge of the rail joint bar.

13. The method of claim 12 wherein said contact with said rail joint bar of said positioning step is completed within six inches of detecting said leading edge of said rail joint bar.

14. The method of claim 12 wherein said contact with said rail joint bar of said positioning step is completed before a point one-half the length of the rail joint bar.

15. The method of claim 12 wherein said contact with said rail joint bar of said positioning step is completed within one half the length of the rail joint bar divided by the speed of the inspection vehicle.

16. The method of claim 12 wherein said contact with said rail joint bar of said positioning step is completed within a range of one half to one quarter the length of the rail joint bar divided by the speed of the inspection vehicle.

17. The method of claim 11 wherein said angle of said ultrasonic beam of said emitting step is approximately 35 degrees to 55 degrees.

18. The method of claim 11 wherein said angle of said ultrasonic beam of said emitting step is approximately 37.5 degrees to 52.5 degrees.

* * * * *